United States Patent
Sato et al.

(10) Patent No.: US 10,223,779 B2
(45) Date of Patent: Mar. 5, 2019

(54) SUPERIMPOSED IMAGE CREATION APPARATUS AND SUPERIMPOSED IMAGE CREATION METHOD

(71) Applicant: HAMAMATSU PHOTONICS K.K., Hamamatsu-shi, Shizuoka (JP)

(72) Inventors: Takayuki Sato, Hamamatsu (JP); Mitsuharu Miwa, Hamamatsu (JP); Kazumasa Hirawake, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 15/557,873

(22) PCT Filed: Feb. 24, 2016

(86) PCT No.: PCT/JP2016/055426
§ 371 (c)(1),
(2) Date: Sep. 13, 2017

(87) PCT Pub. No.: WO2016/147822
PCT Pub. Date: Sep. 22, 2016

(65) Prior Publication Data
US 2018/0082411 A1    Mar. 22, 2018

(30) Foreign Application Priority Data
Mar. 17, 2015    (JP) ................................ 2015-052945

(51) Int. Cl.
*A61B 1/00*    (2006.01)
*A61B 1/04*    (2006.01)
(Continued)

(52) U.S. Cl.
CPC .................. *G06T 5/50* (2013.01); *A61B 1/00* (2013.01); *A61B 1/043* (2013.01);
(Continued)

(58) Field of Classification Search
CPC ............ C12Q 1/6816; C12Q 2563/107; G01N 21/6428; G01N 21/6458
(Continued)

(56) References Cited

U.S. PATENT DOCUMENTS 6,468,204 B2 * 10/2002 Sendai ................ A61B 5/0071
600/108
6,747,281 B2 * 6/2004 Sendai ............... A61B 1/00009
250/458.1
(Continued)

FOREIGN PATENT DOCUMENTS

EP    2754380 A1    7/2014
JP    2009-279172 A    12/2009
(Continued)

OTHER PUBLICATIONS

International Preliminary Report on Patentability dated Sep. 28, 2017 for PCT/JP2016/055426.

*Primary Examiner* — Yosef Kassa
(74) *Attorney, Agent, or Firm* — Drinker Biddle & Reath LLP

(57) ABSTRACT

A fluorescent image acquisition system includes a light emitting device which emits excitation light during ON period and stop the emission of the excitation light during OFF period, an imaging device which outputs ON image data and OFF image data, an input device which sets a coefficient, an image processing unit which creates fluorescent image data and background image data, and an identification unit which identifies fluorescent pixels and non-fluorescent pixels. In order to create a superimposed image, the image processing unit calculates values obtained by summing pixel values of fluorescent pixels of the fluorescent image data and pixel values of fluorescent pixels of the background image data at a ratio of 1:1, as pixel values of the fluorescent pixels and calculates values obtained by (Continued)

multiplying at least pixel values of the non-fluorescent pixels of the background image by the coefficient, as pixel values of the non-fluorescent pixels.

18 Claims, 8 Drawing Sheets

(51) Int. Cl.
 *G06T 5/50* (2006.01)
 *H04N 5/225* (2006.01)
(52) U.S. Cl.
 CPC ........... *G06T 2207/10064* (2013.01); *G06T 2207/10152* (2013.01); *G06T 2207/20221* (2013.01); *H04N 5/2256* (2013.01)
(58) Field of Classification Search
 USPC ............ 382/170, 274, 282, 284, 294, 307; 358/520, 537, 538, 540, 450
 See application file for complete search history.

(56) References Cited

U.S. PATENT DOCUMENTS

| | | | | |
|---|---|---|---|---|
| 7,551,206 B2 * | 6/2009 | Fuyuki | ............... | H04N 9/735 348/223.1 |
| 7,577,284 B2 * | 8/2009 | Wong | ............... | A61B 5/0088 382/128 |
| 8,469,519 B2 * | 6/2013 | Marcus | ............... | G03B 21/567 353/31 |
| 8,593,707 B2 * | 11/2013 | Tanimura | ............ | H04N 1/00846 358/518 |
| 8,731,844 B2 * | 5/2014 | Herzenberg | ....... | G01N 15/1429 702/19 |
| 2011/0042580 A1 | 2/2011 | Wilson et al. | | |
| 2013/0096376 A1 | 4/2013 | Takei et al. | | |

FOREIGN PATENT DOCUMENTS

| | | |
|---|---|---|
| JP | 2012-249804 A | 12/2012 |
| JP | 2013-39275 A | 2/2013 |
| JP | 5355799 B2 | 11/2013 |
| WO | WO-2013/015120 A1 | 1/2013 |
| WO | WO 2015/025640 A1 | 2/2015 |

\* cited by examiner

SUPERIMPOSED IMAGE CREATION APPARATUS AND SUPERIMPOSED IMAGE CREATION METHOD

TECHNICAL FIELD

The present invention relates to a superimposed image creation apparatus and a superimposed image creation method for creating an image in which a background image is superimposed on a fluorescent image of an object to be measured.

BACKGROUND ART

Observation devices for observing a fluorescent image generated in accordance with emission of excitation light from a living body or the like have been used conventionally. In such observation devices, an image obtained by capturing a reflected image generated by illumination light and an image obtained by capturing the fluorescent image generated by the excitation light are superimposed. For example, the following Patent Literature 1 describes a configuration in which a balance between a fluorescent image and a reflected image is adjusted by superimposing image data of a binned fluorescent image and image data of a reflected image. Also, in the following Patent Literature 2, a process of creating an image of a fluorescent image by assigning data to which an estimated fluorescence yield or the like is added to a pixel value and outputting an observation image by superimposing the image and a reflected image is described.

CITATION LIST

Patent Literature

[Patent Literature 1] Japanese Patent No. 5355799
[Patent Literature 2] Japanese Unexamined Patent Publication No. 2009-279172

SUMMARY OF INVENTION

Technical Problem

However, in the devices described in the above-described Patent Literatures 1 and 2, superimposition is performed by generally adjusting a balance between an image obtained by capturing a fluorescent image and an image obtained by capturing a background image. Thus, it may be difficult to recognize the fluorescent image itself in a superimposed image when luminance of the fluorescent image is low.

Therefore, the present invention has been made in view of such a problem, and an objective of the invention is to provide a superimposed image creation apparatus and a superimposed image creation method for further facilitating recognition of a fluorescent image in a superimposed image in which the fluorescent image and a background image are superimposed.

Solution to Problem

To solve the above-described problem, a superimposed image creation apparatus according to an embodiment of the present invention is an apparatus for creating a fluorescent image by imaging fluorescence emitted from an object and creating a superimposed image by superimposing a background image on the fluorescent image, the apparatus including: a light irradiating unit for emitting excitation light toward the object during a first period and stopping the emission of the excitation light during a second period different from the first period; a capturing unit having a plurality of pixels that are two-dimensionally arranged and for outputting first image data and second image data by capturing image of the object during each of the first period and the second period; a coefficient setting unit for setting a coefficient for adjusting a luminance value of the background image in the superimposed image; an image processing unit for creating fluorescent image data including the fluorescent image and background image data including the background image on the basis of the first image data and the second image data; and an identification unit for identifying fluorescent pixels, which are pixels constituting the fluorescent image, and non-fluorescent pixels, which are pixels other than the fluorescent pixels, among the plurality of pixels using the fluorescent image data, wherein the image processing unit is configured to calculate values, which are obtained by summing pixel values of the fluorescent pixels of the fluorescent image data and pixel values of the fluorescent pixels of the background image data at a ratio of 1:1, as pixel values of the fluorescent pixels of the superimposed image and calculate values, which are obtained by multiplying at least pixel values of the non-fluorescent pixels of the background image data by the coefficient, as pixel values of the non-fluorescent pixels of the superimposed image to create the superimposed image.

Alternatively, a superimposed image creation method according to another embodiment of the present invention is a method of creating a fluorescent image by imaging fluorescence emitted from an object and creating a superimposed image by superimposing a background image on the fluorescent image, the method including the steps of: emitting excitation light toward the object during a first period and stopping the emission of the excitation light during a second period different from the first period (an emission step); outputting first image data and second image data by capturing image of the object during each of the first period and the second period using an image sensor having a plurality of pixels that are two-dimensionally arranged (an output step); setting a coefficient for adjusting a luminance value of the background image in the superimposed image (a setting step); creating fluorescent image data including the fluorescent image and background image data including the background image on the basis of the first image data and the second image data (a creation step); identifying fluorescent pixels, which are pixels constituting the fluorescent image, and non-fluorescent pixels, which are pixels other than the fluorescent pixels, among the plurality of pixels using the fluorescent image data (an identification step); and calculating values, which are obtained by summing pixel values of the fluorescent pixels of the fluorescent image data and pixel values of the fluorescent pixels of the background image data at a ratio of 1:1, as pixel values of the fluorescent pixels of the superimposed image and calculating values, which are obtained by multiplying at least pixel values of the non-fluorescent pixels of the background image data by the coefficient, as pixel values of the non-fluorescent pixels of the superimposed image to create the superimposed image (a calculation step).

According to the superimposed image creation apparatus or the superimposed image creation method of the above-described embodiment, the first image data is acquired by capturing image of the object in the first period during which the excitation light is emitted toward the object, the second image data is acquired by capturing image of the object in the second period during which no excitation light is emitted toward the object, and the fluorescent image data to which the fluorescent image is applied and the background image data to which the background image is applied are created on the basis of the first and second image data. Further, the fluorescent pixels constituting the fluorescent image and the non-fluorescent pixels other than the fluorescent pixels are identified among the plurality of pixels of the fluorescent image data, and the superimposed image is created so that values, which are obtained by summing pixel values of the fluorescent pixels of the fluorescent image data and pixel values of the fluorescent pixels of the background image data at a ratio of 1:1, are designated as the pixel values of the fluorescent pixels and values, which are obtained by multiplying at least pixel values of the non-fluorescent pixels of the background image data by the coefficient, are designated as the pixel values of the non-fluorescent pixels. According to this configuration, it is possible to relatively adjust luminance of the background image with respect to luminance of the fluorescent image in the superimposed image, conspicuously maintain the luminance of the fluorescent image with respect to the background image, and more easily recognize the fluorescent image in the superimposed image.

Advantageous Effects of Invention

According to a form of the present invention, it is possible to further facilitate recognition of a fluorescent image in a superimposed image in which the fluorescent image and a background image are superimposed.

DESCRIPTION OF EMBODIMENTS

Figure 1:
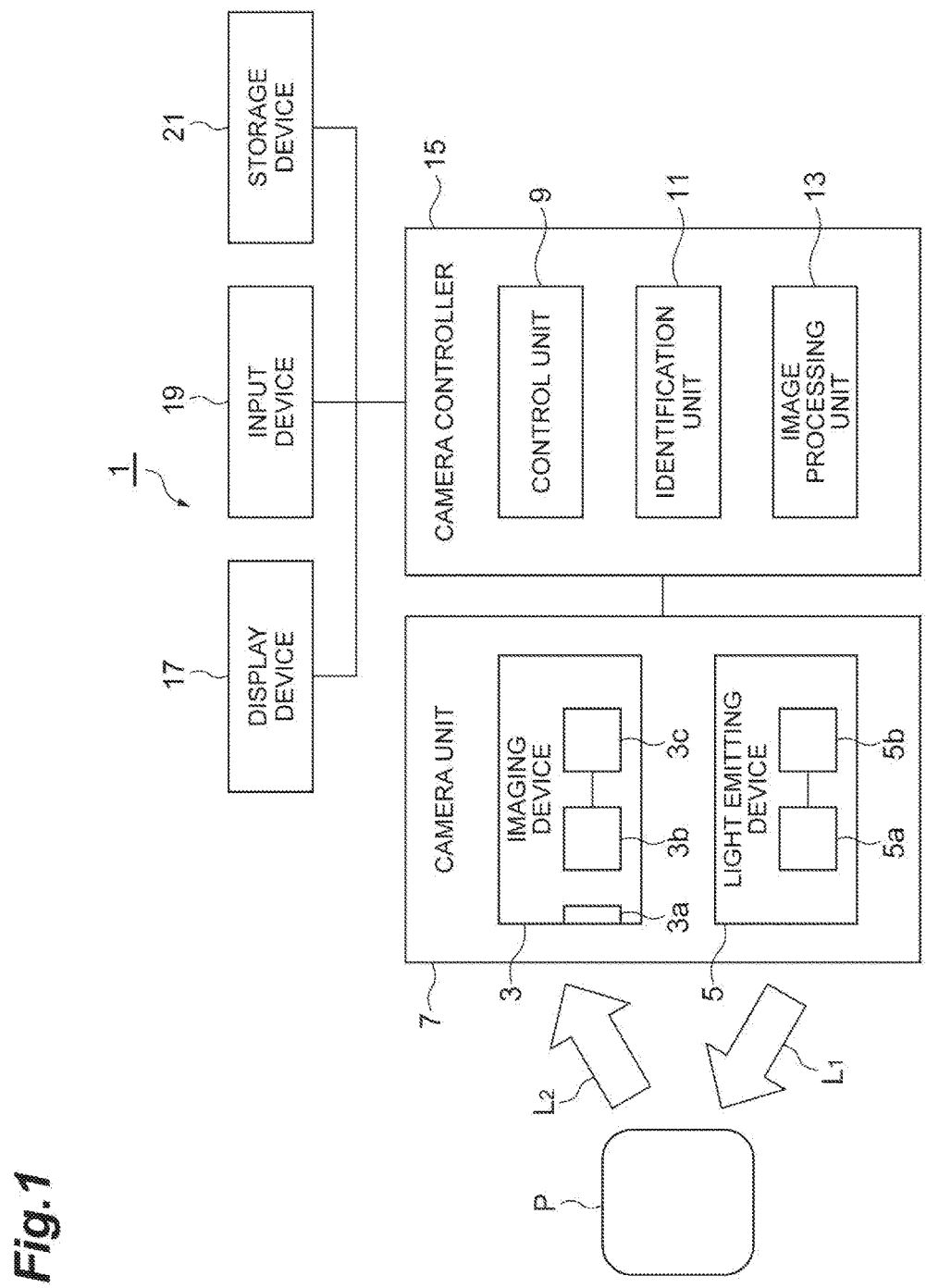
FIG. 1 is a block diagram illustrating a schematic configuration of a fluorescent image acquisition system 1 according to a preferred embodiment of the present invention.

Hereinafter, preferred embodiments of a superimposed image creation apparatus and a superimposed image creation method according to the present invention will be described in detail with reference to the accompanying drawings. In the description of the drawings, the same or corresponding parts are denoted by the same reference numerals, and redundant descriptions thereof will be omitted.

FIG. 1 is a block diagram illustrating a schematic configuration of a fluorescent image acquisition system 1 according to a preferred embodiment of the present invention. The fluorescent image acquisition system 1 illustrated in FIG. 1 is configured so that a user can observe an observation object P in a moving image by acquiring observation images of the observation object P in a time series at a predetermined frame rate. The observation object P is, for example, a biological tissue to which a fluorescent dye, such as indocyanine green, has been introduced in advance. If the fluorescent image acquisition system 1 is used, it is possible to observe how the fluorescent dye flows through blood vessels, lymph vessels, and the like of a living body and how a fluorescent pigment is accumulated in organs and lymph nodes in the living body. The fluorescent image acquisition system 1, which is one form of superimposed image creation apparatus, includes a camera unit 7 having an imaging device (capturing unit) 3 and a light emitting device (light irradiating unit) 5 built therein, a camera controller 15 electrically connected to the camera unit 7 and having a control unit 9 for controlling the camera unit 7 and an identification unit 11 and an image processing unit 13 for processing image data output from the camera unit 7, and a display device 17, an input device 19, and a storage device 21 electrically connected to the camera controller.

The light emitting device 5 includes a light source 5a that emits excitation light $L_1$ for exciting a fluorescent dye for fluorescence observation of the observation object P and a light source control unit 5b that controls ON/OFF of the emission of the excitation light $L_1$ of the light source 5a built therein. The light source 5a is a light emitting element such as a light emitting diode (LED), a laser diode (LD), or a super luminescent diode (SLD) and emits light having a wavelength that excites a fluorescent dye. The light source control unit 5b is a control circuit that alternately and iteratively switches ON (an output state) and OFF (an output stop state) of the excitation light emission of the light source 5a under the control of the camera controller 15 electrically connected to the camera unit 7. Also, it is preferable that the wavelength of the light emitted from the light source 5a not include a wavelength of fluorescence. If the wavelength of the light emitted from the light source 5a includes the wavelength of fluorescence, the light emitting device 5 may include an optical filter (not illustrated) that blocks light having the same wavelength as the wavelength of the fluorescence of light emitted from the light source 5a.

The imaging device 3 is a device for capturing an optical image of the observation object P under the control of the camera controller 15. The imaging device 3 is configured to include an optical filter 3a that passes light of a wavelength of fluorescence $L_2$ emitted from the fluorescent dye and blocks light of a wavelength of the excitation light $L_1$, an image sensor 3b that receives the fluorescence $L_2$ passing through the optical filter 3a and background light, which is light from a background of a fluorescent image of the observation object P, and outputs image data by photoelectrically converting the light, and an imaging control unit 3c that adjusts an exposure timing and an exposure time of the image sensor 3b under the control of the camera controller 15. The image sensor 3b is an area image sensor such as a CCD image sensor or a CMOS image sensor, and includes a plurality of pixels (photoelectric conversion elements) that are two-dimensionally arranged. The optical filter 3a is configured to pass not only light having the wavelength of the fluorescence $L_2$ but also light of a wavelength of reflected light generated in the observation object P by illumination light emitted from an external illumination device. Thus, the image sensor 3b receives reflected light from the observation object P as background light.

In the camera unit 7 having the above-described configuration, the image sensor 3b receives (images) the fluorescence from the observation object P and the background light, and outputs ON image data as image data in accordance with the received (imaged) fluorescence and background light in a period during which the excitation light emission of the light source 5a is ON (hereinafter simply referred to as an "ON period"). On the other hand, the image sensor 3b receives (images) the background light from the observation object P and outputs OFF image data as image data in accordance with the received (imaged) background light in a period during which the excitation light emission of the light source 5a is OFF (hereinafter simply referred to as an "OFF period"). If the frame rate of the image data output from the camera unit 7 is set to, for example, 30 frames/sec, the imaging control unit 3c performs control so that the exposure time is, for example, 30 msec. If the frame rate is adjusted within a range of 15 frames/sec to 1000 frames/sec according to a setting change of the camera unit 7, the imaging control unit 3c performs control so that the exposure time is variable within a range of 60 msec to 1 msec in accordance therewith.

The camera controller 15 is a data processing device including an arithmetic processing circuit such as a field programmable gate array (FPGA) or a central processing unit (CPU), a memory, and the like, and the control unit 9, the identification unit 11, and the image processing unit 13 are functionally mounted in the data processing device. However, the control unit 9, the identification unit 11, and the image processing unit 13 are not limited to the case in which they are configured within the same device, and may be configured to be distributed in a plurality of devices.

The control unit 9 of the camera controller 15 controls operations of the imaging device 3 and the light emitting device 5. That is, the control unit 9 controls ON/OFF of the excitation light emission by the light emitting device 5 and the exposure timing of the image sensor 3b so that they are synchronized (details thereof will be described below). The image processing unit 13 of the camera controller 15 performs image processing on the ON image data and the OFF image data output from the image sensor 3b to create fluorescent image data, which includes a fluorescent image to which a fluorescence distribution is applied among optical images from the observation object P, and background image data, which includes a background image to which a background distribution is applied among the optical images from the observation object P. Specifically, the image processing unit 13 calculates a difference at the same pixel position of each piece of image data between the ON image data and the OFF image data ("ON image data"-"OFF image data") to create the fluorescent image data. Also, the image processing unit 13 creates the background image data using the OFF image data as it is. Further, the image processing unit 13 uses the fluorescent image data and the background image data to create superimposed image data to which an image, in which the background image from the observation object P and the fluorescent image from the observation object P are superimposed, is applied, and outputs the created superimposed image data as output image data to the display device 17 and the storage device 21 (details of the superimposed image creation method will be described below). Using the fluorescent image data created by the image processing unit 13, the identification unit 11 of the camera controller 15 identifies fluorescent pixels, which are pixels constituting a fluorescent image, and background pixels (non-fluorescent pixels), which are pixels other than the fluorescent pixels, among a plurality of pixels included in the image data (details of the pixel identification method will be described below). Then, the identification unit 11 delivers information about the identified pixels to the image processing unit 13.

The display device 17 is an image output device such as a display device connected to the camera controller 15 and displays display image data output from the image processing unit 13. Also, the input device 19 is a data input device such as a keyboard, a mouse, or a touch panel display connected to the camera controller 15 and inputs parameters for designating imaging conditions in the camera unit 7 and parameters indicating conditions of image processing in the image processing unit 13. Also, the function of the input device 19 may be provided in the camera unit 7 or the camera controller 15 by providing a button or the like in the camera unit 7 or the camera controller 15. For example, the input device 19 receives setting inputs of an exposure time of the imaging device 3, an emission intensity of the light emitting device 5, and a coefficient m indicating an adjustment ratio of a pixel value of the background image when the superimposed image is created in the image processing unit 13. Further, the input device 19 sets the received parameters in the camera controller 15. That is, the input device 19 functions as a coefficient setting unit that sets the coefficient m. Also, the storage device 21 is a data storage device connected to the camera controller 15 and stores display image data, various types of image data that are processed by the camera controller 15, and various types of parameters that are set by the input device 19.

Figure 2:
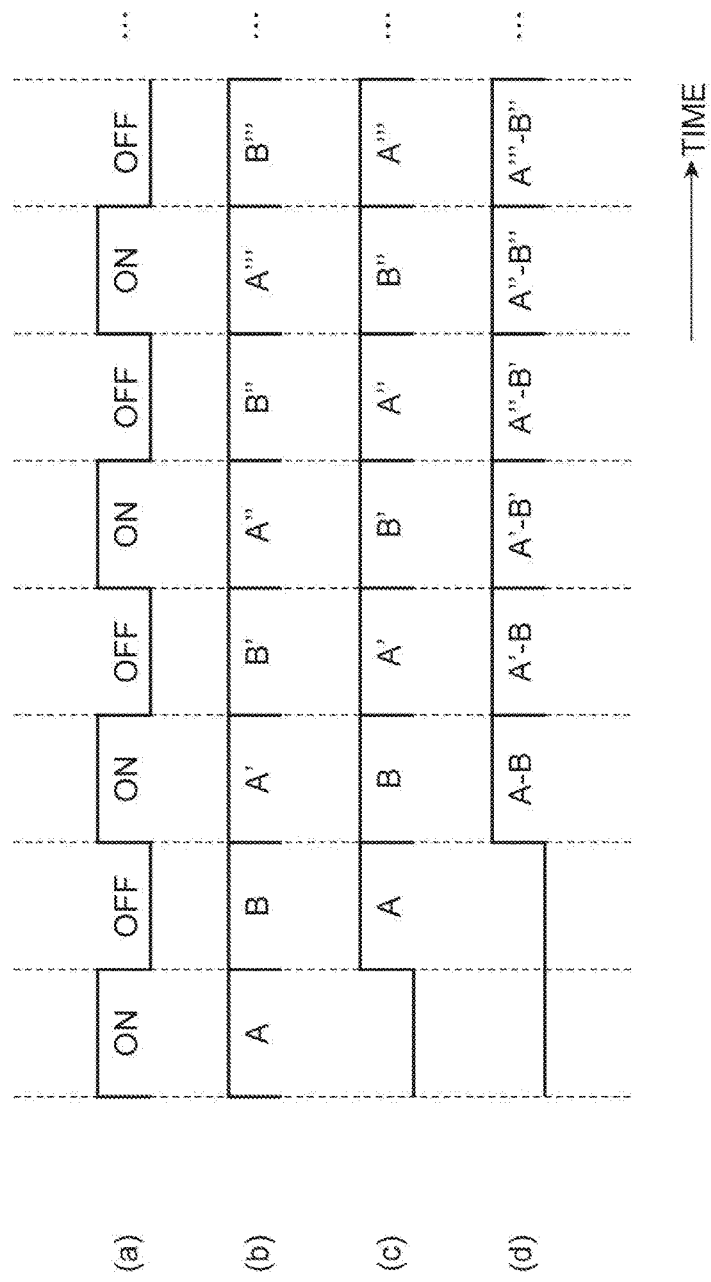
FIG. 2 is a timing chart illustrating timings of various operations controlled by a camera controller 15 of FIG. 1.

Here, a temporal relationship of an ON/OFF timing of the excitation light emission of the light source 5a, the exposure timing of the image sensor 3b, and a creation timing of the fluorescent image data by the image processing unit 13 will be described with reference to FIG. 2. FIG. 2 is a timing chart illustrating timings of various operations controlled by the camera controller 15. Part (a) in FIG. 2 illustrates an ON/OFF timing of the excitation light emission of the light source 5a, part (b) in FIG. 2 illustrates the exposure timing of the image sensor 3b, part (c) in FIG. 2 illustrates a saving timing of the image data of the image processing unit 13, and part (d) in FIG. 2 illustrates the creation timing of the fluorescent image data of the image processing unit 13.

As illustrated in parts (a) and (b) in FIG. 2, the control unit 9 controls the ON/OFF timing of the excitation light of the light source 5a so that the ON period and the OFF period are alternately iterated in synchronization with an exposure period of one frame of the image sensor 3b. That is, a length of the ON period and a length of the OFF period are substantially the same as a length of the exposure period, and the OFF period is set to be a period different from the ON period. Then, the image processing unit 13 acquires image data output on the basis of an electric charge accumulated in accordance with an exposure of the image sensor 3b in the ON period as ON image data A. Thereafter, the image processing unit 13 acquires image data output on the basis of an electric charge accumulated in accordance with an exposure of the image sensor 3b in the subsequent OFF period as OFF image data B. At this time, the first ON image data A is stored in the memory in the image processing unit 13 at a time of acquisition, and then OFF image data B acquired thereafter is input to a difference circuit in the image processing unit 13 and saved in the memory. The ON image data A in the memory is also input to the difference circuit at a timing at which the OFF image data B is input to the difference circuit so that a difference between the two pieces of image data is calculated and fluorescent image data A-B is created. Subsequently, subsequently obtained ON image data A' is input to the difference circuit and saved in the memory. The OFF image data B in the memory is also input to the difference circuit at a timing at which the ON image data A' is input to the difference circuit so that a difference between the two pieces of image data is calculated and fluorescent image data A'-B is created. By iterating such processing, the image processing unit 13 can acquire time-series fluorescent image data for each exposure period (frame) of the image sensor 3b.

Figure 3:
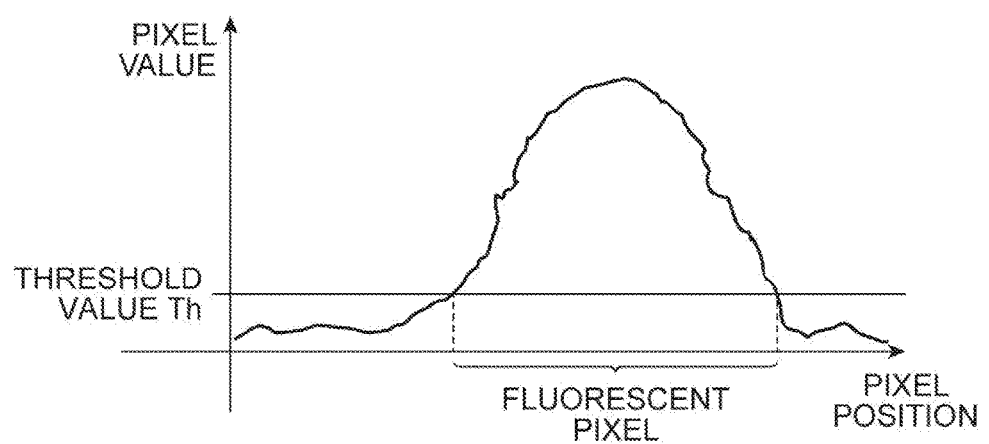
FIG. 3 is a graph illustrating a one-dimensional distribution of pixel values of fluorescent image data of a processing object of an identification unit 11 of FIG. 1.

Next, details of the pixel identification process performed by the identification unit 11 of the camera controller 15 will be described. FIG. 3 is a graph illustrating a one-dimensional distribution of pixel values of fluorescent image data to be processed by the identification unit 11 and FIGS. 4 and 5 are graphs illustrate histograms of luminance values of image data calculated by the identification unit 11.

With respect to fluorescent image data having a one-dimensional distribution of pixel values illustrated in FIG. 3, the identification unit 11 compares a pixel value of each pixel of the fluorescent image data with a preset threshold value Th to determine whether the pixel is a fluorescent pixel or a background pixel. Specifically, a pixel having a pixel value larger than the threshold value Th is identified as a fluorescent pixel, and a pixel having a pixel value smaller than or equal to the threshold value is identified as a background pixel. The threshold value Th is preset for each fluorescent image data in the following process so that the threshold value Th has a luminance value larger than a background noise level of the fluorescent image data.

Figure 4:
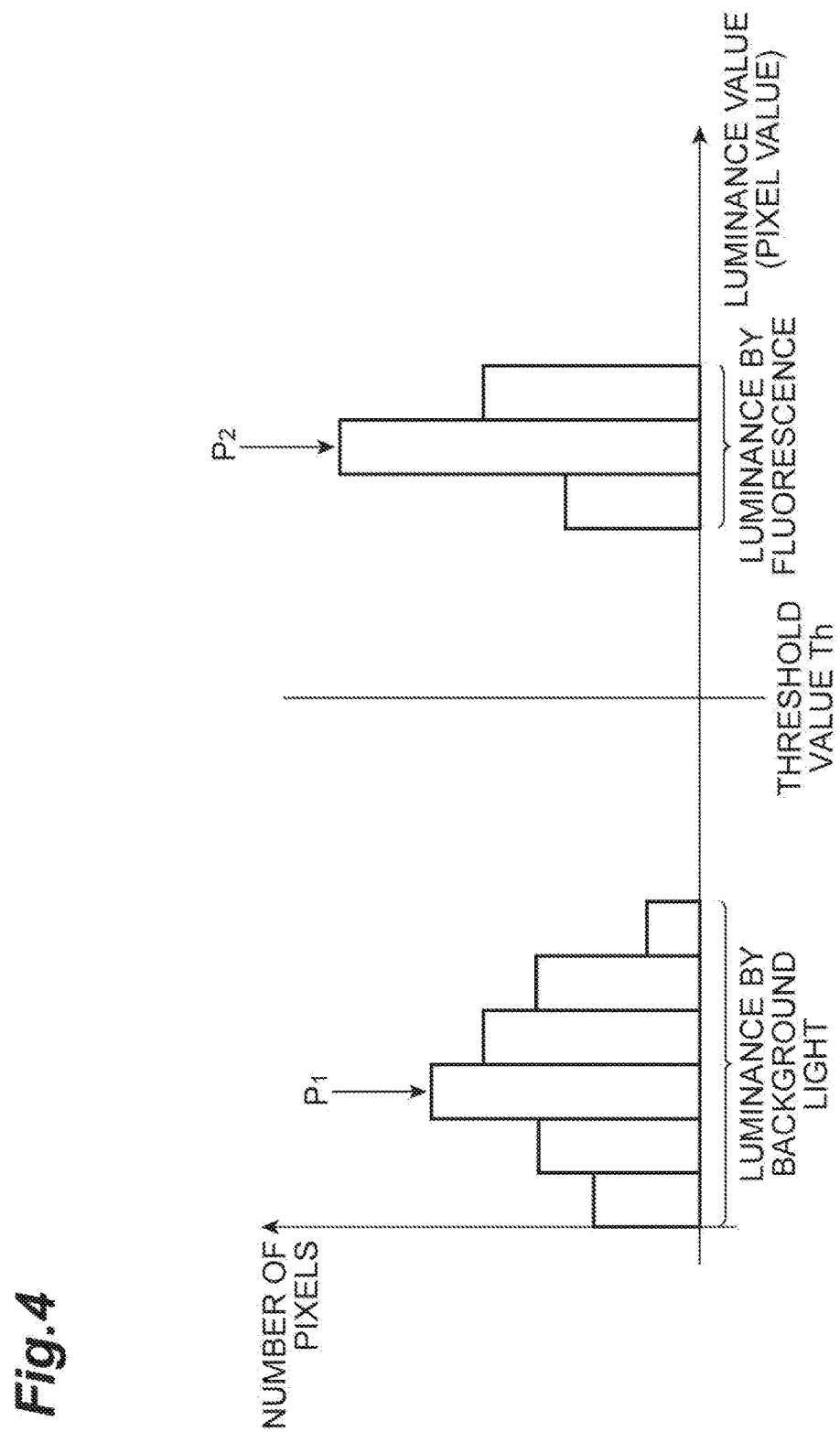
FIG. 4 is a graph illustrating a histogram of a luminance value of ON image data calculated by the identification unit 11 of FIG. 1.
Figure 5:
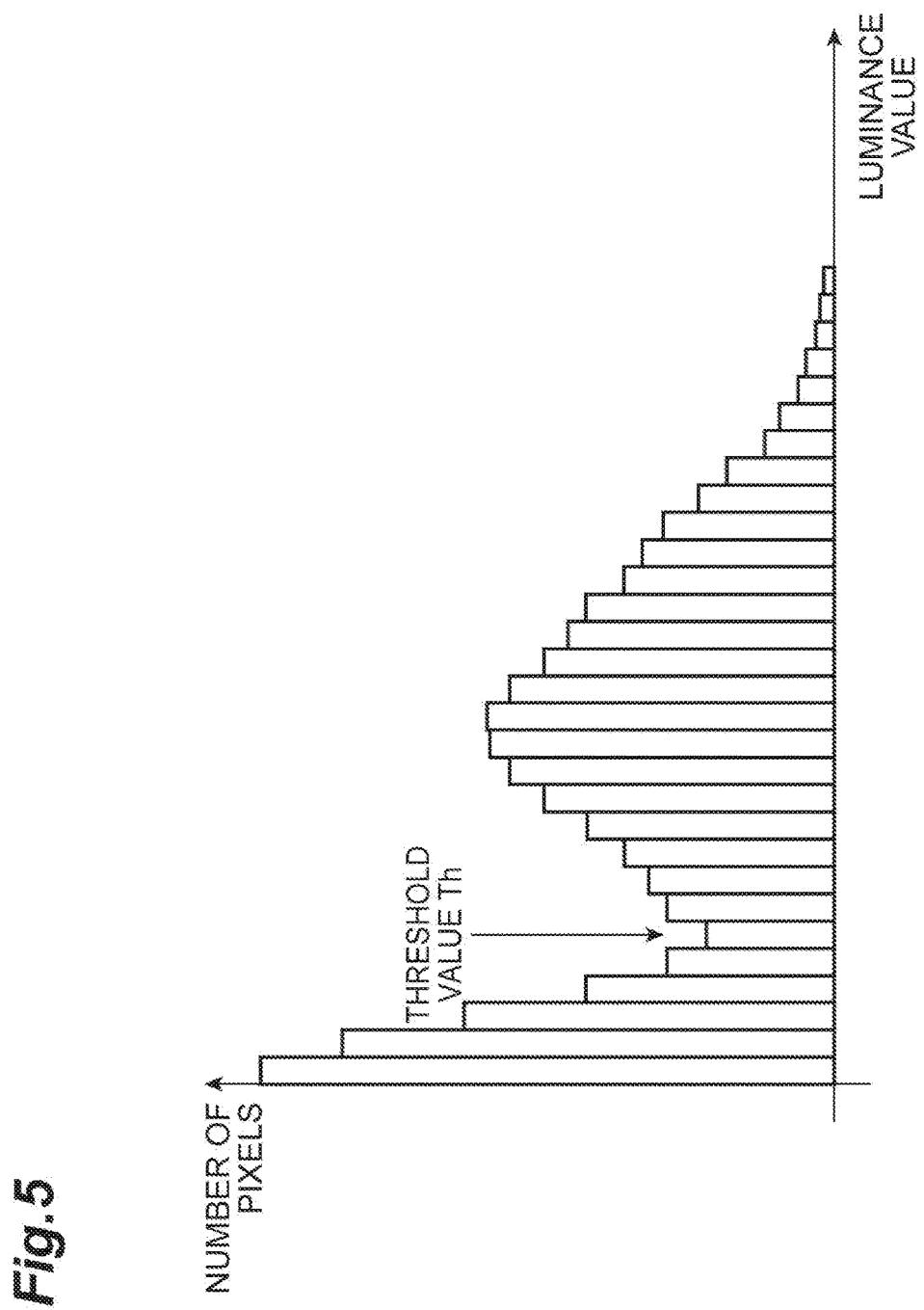
FIG. 5 is a graph illustrating a histogram of a luminance value of fluorescent image data calculated by the identification unit 11 of FIG. 1.

That is, the identification unit 11 calculates a histogram of pixel values of ON image data used for creating fluorescent image data to be processed (FIG. 4). Then, the identification unit 11 identifies a peak $P_1$ of a luminance value distribution of background light and a peak $P_2$ of a luminance value distribution of fluorescence, and sets the threshold value Th so that the threshold value Th becomes an intermediate luminance value between the peaks $P_1$ and $P_2$.

Further, the identification unit 11 may set the threshold value Th by the following processing. That is, the identification unit 11 calculates a histogram of pixel values of fluorescent image data to be processed (FIG. 5). Then, the identification unit 11 may identify the bottom of the luminance value distribution in the histogram and set the threshold value Th so that the threshold value Th becomes a luminance value at the bottom.

Next, details of a superimposed image data creation method by the image processing unit 13 will be described.

The image processing unit 13 creates superimposed image data using the coefficient m indicating an adjustment ratio of a pixel value of a background image input from the input device 19. If a pixel value of a fluorescent image in fluorescent image data is larger than the pixel value of the background image in the background image data, that is, if luminance of the fluorescent image is higher than luminance of the background image, this coefficient m is set to $0 \le m \le 1$. By using such a coefficient m, a pixel value of a background pixel of the superimposed image data becomes a value obtained by summing a pixel value of a background pixel of the fluorescent image data and a value obtained by multiplying a pixel value of a background pixel of the background image data by the coefficient m. On the other hand, a pixel value of a fluorescent pixel of the superimposed image data becomes a value obtained by summing a pixel value of a fluorescent pixel of the fluorescent image data and a pixel value of a fluorescent pixel of the background image data at a ratio of 1:1. Thereby, in the superimposed image data, luminance of the background light can be lowered in accordance with the coefficient m in a background portion of the fluorescent image, and luminance of the fluorescence and the luminance of the background light can be superimposed at a ratio of 1:1 in a fluorescent image portion.

More specifically, the image processing unit 13 calculates the following equation on the basis of background image data $I_b(x, y)$ (x and y are two-dimensional coordinates of a pixel on image data and $I_b$ indicates a pixel value of each pixel) and the coefficient m to calculate each pixel value $I_B(x, y)$ of the background image data of a superimposition source.

$$I_B(x,y)=I_b(x,y)\times m$$

That is, the background image data of the superimposition source is created by multiplying the pixel values $I_b(x, y)$ of all of the pixels including the fluorescent pixel and the background pixel of the background image data by the coefficient m.

Subsequently, the image processing unit 13 calculates the following equation on the basis of fluorescent image data $I_f(x, y)$, the background image data $I_b(x, y)$, and the coefficient m to calculate each pixel value $I_F(x, y)$ of the fluorescent image data of the superimposition source.

$$I_F(x,y)=I_f(x,y)+n\times(I_b(x,y)\times(1-m))$$

Here, the parameter n in the above-described equation is assigned n=1 in the fluorescent pixel and n=0 in the background pixel, and is set on the basis of a result of a pixel identification process by the identification unit 11. That is, the pixel value $I_f(x, y)$ of each pixel of the fluorescent image data and a pixel value of a fluorescent pixel of the background image data $I_b(x, y)$ whose ratio (1−m) is adjusted so that the pixel value increases in accordance with a decreasing rate of luminance indicated by the coefficient m are summed to create the fluorescent image data of the superimposition source. Thereby, it is possible to compensate for a decrease in the pixel value of the background image data of the superimposition source in the fluorescent pixel by using the pixel value of the fluorescent image data of the superimposition source.

Further, the image processing unit 13 creates superimposed image data by superimposing the background image data of the superimposition source and the fluorescent image data of the superimposition source. Specifically, the pixel value $I_B(x, y)$ of each pixel of the background image data of the superimposition source and each of the pixel values $I_F(x, y)$ of the fluorescent image data of the superimposition source are summed. Thereby, a pixel value $I_{Sf}(x, y)$ of the superimposed image data in the fluorescent pixel is set by a value calculated by the following equation.

$$I_{Sf}(x,y)=I_b(x,y)+I_f(x,y)$$

The background image and the fluorescent image are superimposed at a luminance ratio of 1:1. On the other hand, the pixel value $I_{Sf}(x, y)$ of the superimposed image data in the background pixel is set by a value calculated by the following equation.

$$I_{Sf}(x,y)=I_b(x,y)\times m+I_f(x,y)\approx I_b(x,y)\times m$$

The luminance of the background image is lowered corresponding to the coefficient m. Here, the luminance value $I_f(x, y)$ in the background pixel is a noise level and becomes a negligible value.

Figure 6:
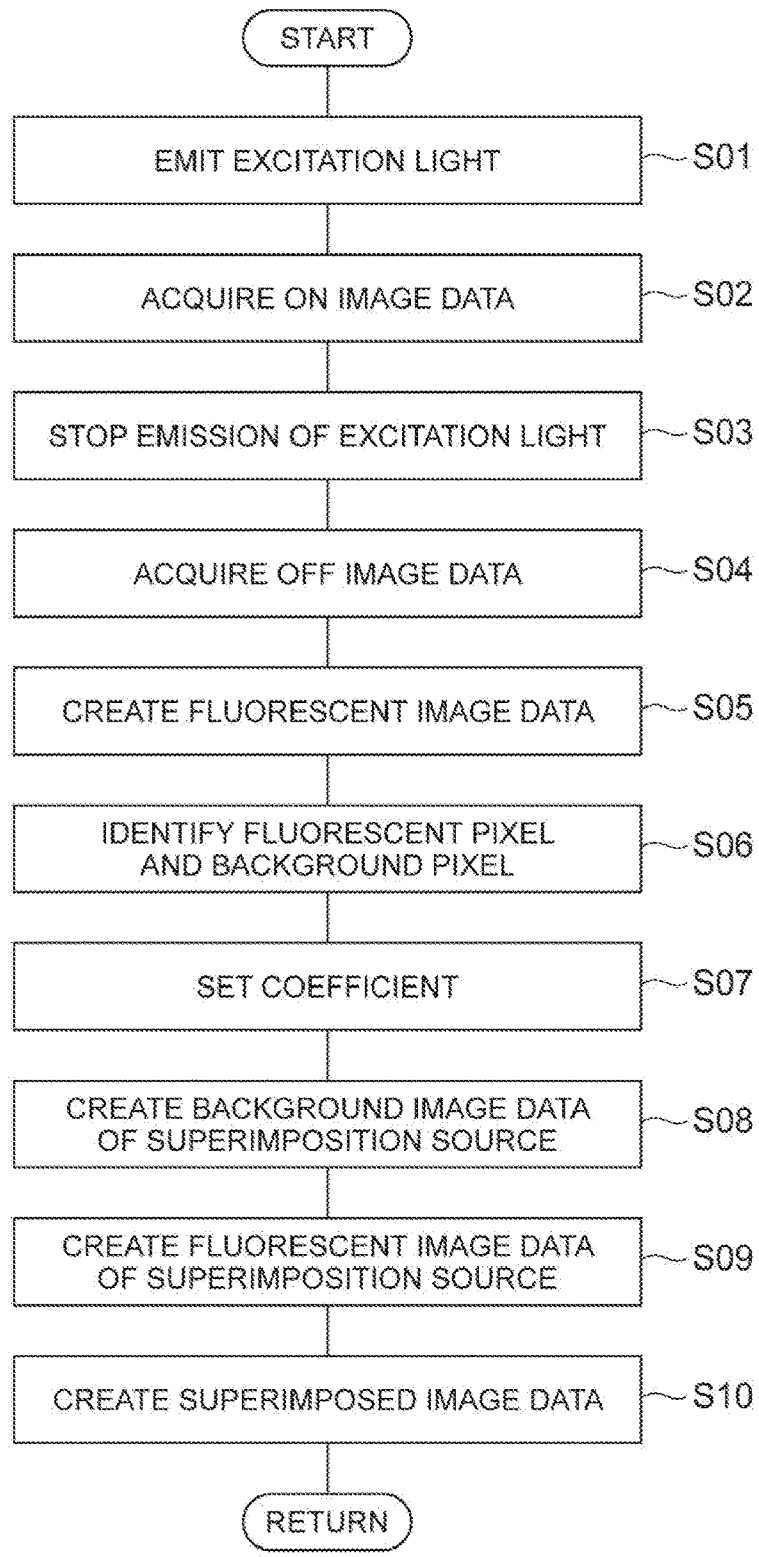
FIG. 6 is a flowchart illustrating a procedure of a superimposed image data creation process by the fluorescent image acquisition system 1 of FIG. 1.

Hereinafter, a procedure of the superimposed image data creation process by the above-described fluorescent image acquisition system 1 will be described and the superimposed image data creation method of the present embodiment will be described in detail. FIG. 6 is a flowchart illustrating a superimposed image data creation process by the fluorescent image acquisition system 1. In the fluorescent image acquisition system 1, a superimposed image of the observation object P is configured to be acquired in time series by iterating the process illustrated in FIG. 6.

Figure 7:
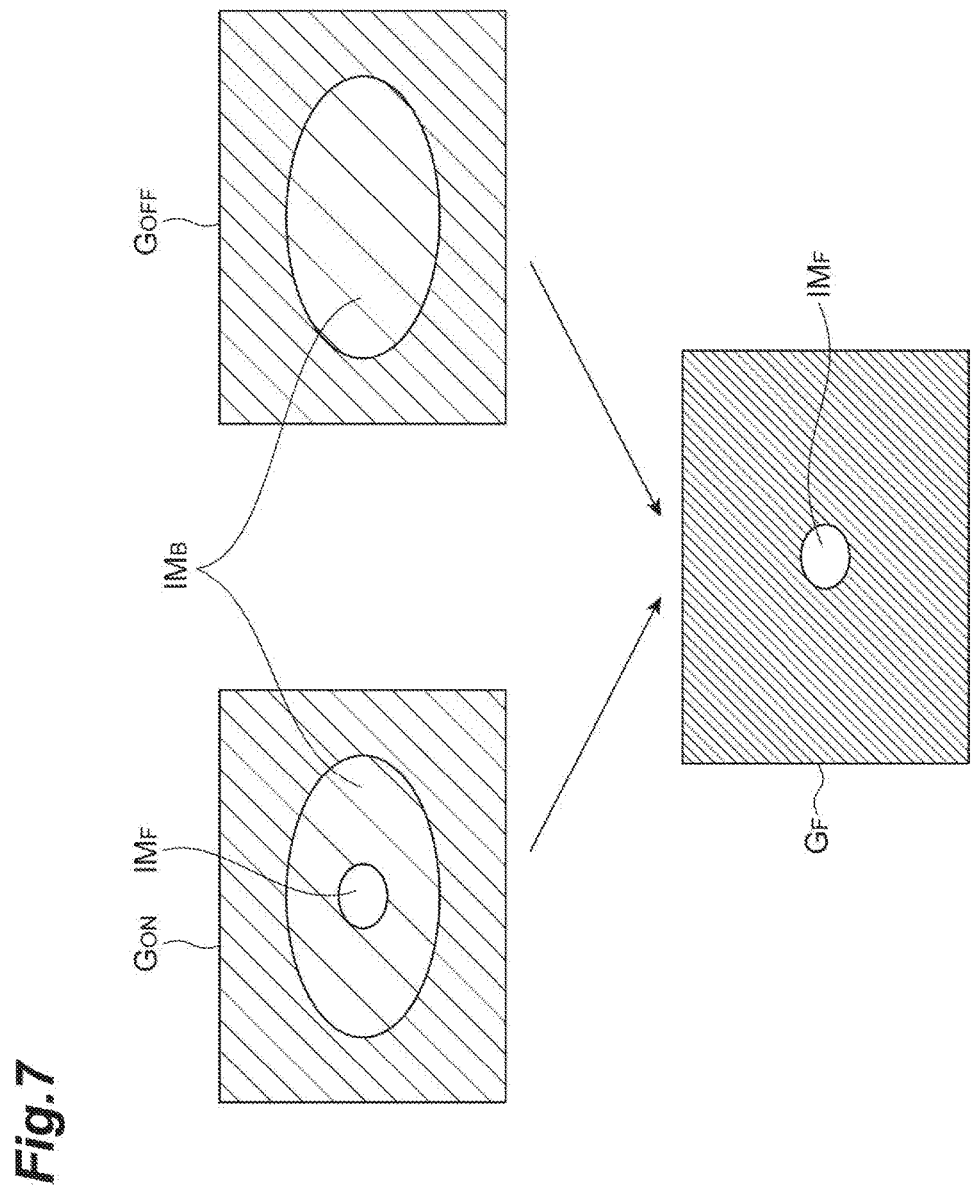
FIG. 7 is a diagram illustrating images of ON image data, OFF image data, and fluorescent image data created by the fluorescent image acquisition system 1 of FIG. 1.

First, when the superimposed image acquisition process is started by an instruction input by a user, excitation light from the light source 5a is emitted toward the observation object P to which a fluorescent dye is introduced at a timing (during an ON period) synchronized with an exposure period of the image sensor 3b (step S01: an emission step). In synchronization with this, ON image data is acquired from the imaging device 3 by the image processing unit 13 (step S02: an output step). Subsequently, the emission of the excitation light from the light source 5a is stopped (step S03: an emission step) at a timing (during an OFF period) synchronized with a next exposure period of the image sensor 3b. In synchronization with this, OFF image data is acquired from the imaging device 3 by the image processing unit 13 (step S04: an output step). Thereafter, the image processing unit 13 calculates a difference between the ON image data and the OFF image data ("ON image data"-"OFF image data") to create fluorescent image data (step S05). FIG. 7 is a diagram illustrating images $G_{ON}$, $G_{OFF}$, and $G_F$ of the ON image data, the OFF image data, and the fluorescent image data created by the fluorescent image acquisition system 1, respectively. By taking a difference between the ON image $G_{ON}$ including a fluorescent image $IM_F$ and a background image $IM_B$ and the OFF image $G_{OFF}$ including the background image $IM_B$ as described above, it is possible to obtain fluorescent image data to which the fluorescent image $IM_F$ is applied.

Next, the identification unit 11 identifies fluorescent pixels and background pixels among the pixels in the image data using the fluorescent image data (step S06: an identification step). Also, the coefficient m for creating superimposed image data is set according to reading from the memory by the image processing unit 13 (step S07: a setting step). Subsequently, the image processing unit 13 creates background image data of a superimposition source on the basis of the background image data and the coefficient m (step S08: a calculation step). In addition, the image processing unit 13 creates fluorescent image data of the superimposition source on the basis of the background image data, the fluorescent image data, and the coefficient m (step S09: a calculation step). Finally, the background image data of the superimposition source and the fluorescent image data of the superimposition source are superimposed by the image processing unit 13 to create the superimposed image data (step S10: a calculation step). The superimposed image data is displayed on the display device 17.

According to the above-described fluorescent image acquisition system 1, ON image data is acquired by capturing image of the observation object P in the ON period during which fluorescence is excited from the observation target P, and OFF image data is acquired by capturing image of the observation object P in the OFF period during which emission of the excitation light to the observation object P is stopped. On the basis of the ON image data and the OFF image data, fluorescent image data to which the fluorescent image is applied and background image data to which the background image is applied are created. Further, fluorescent pixels constituting the fluorescent image and background pixels other than the fluorescent pixels are identified among the plurality of pixels of the fluorescent image data. Thereafter, a superimposed image in which values, which are obtained by summing pixel values of the fluorescent pixels of the fluorescent image data and pixel values of the fluorescent pixels of the background image data at a ratio of 1:1, are designated as pixel values of the fluorescent pixels and values, which are obtained by adding values obtained by multiplying pixel values of background pixels of the background image data by the coefficient m to pixel values of background pixels of the fluorescent image data, are designated as pixel values of the background pixels is created. Generally, there is a technique of increasing luminance of a fluorescent image as a technique of making a fluorescent image conspicuous with respect to a background image. However, this technique has a problem in that a distribution of a fluorescent dye may not be properly ascertained. On the other hand, according to the configuration of the fluorescent image acquisition system 1, it is possible to relatively adjust the luminance of the background image in accordance with the coefficient m with respect to the luminance of the fluorescent image, and maintain the luminance of the fluorescent image in the superimposed image. As a result, it is possible to evaluate an appropriate fluorescent image while highlighting the fluorescent image with respect to the background image, and it is possible to more easily recognize the fluorescent image in the superimposed image. Also, the pixel value of the pixel of the fluorescent image data is applied to the background pixel in the superimposed image. Thereby, it is possible to improve minuteness of the image in the vicinity of a boundary of the fluorescent image.

Figure 8:
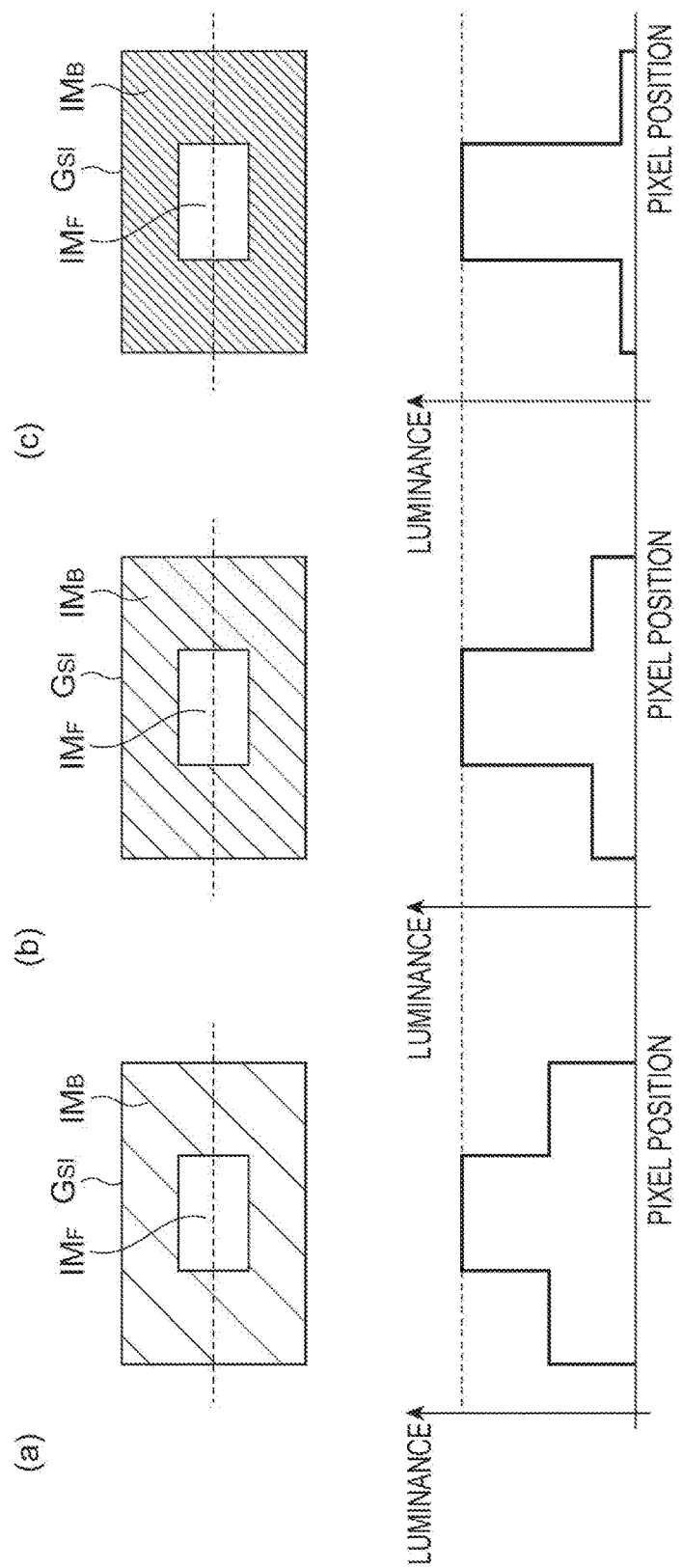
FIG. 8 is a diagram illustrating an image of superimposed image data created by the fluorescent image acquisition system 1 and a one-dimensional luminance distribution of superimposed image data thereof when a coefficient m is set to various values.

Also, because the coefficient m is set to $0 \le m \le 1$, it is possible to maintain the luminance of the fluorescent image while making the fluorescent image conspicuous with respect to the background image if the fluorescent image having a high pixel value (luminance) with respect to the background image is used. In FIG. 8, images of superimposed image data created by the fluorescent image acquisition system 1 with respect to the same observation object P under the same imaging conditions and one-dimensional luminance distributions of the superimposed image data when the coefficient m is set to various values are illustrated. An image of superimposed image data created when the coefficient m=1 and a luminance distribution of a one-dimensional direction of pixels in a dotted line direction of the superimposed image data are illustrated in part (a) of FIG. 8. An image of superimposed image data created when the coefficient m=½ and a luminance distribution of a one-dimensional direction in a dotted line direction of the superimposed image data are illustrated in part (b) of FIG. 8. An image of superimposed image data created when the coefficient m=¼ and a luminance distribution of a one-dimensional direction in a dotted line direction of the superimposed image data are illustrated in part (c) of FIG. 8. Because a ratio of luminance of background light in a superimposed image can be adjusted in accordance with the coefficient m as described above, it is easy to recognize the fluorescent image $IM_F$. On the other hand, because luminance of the fluorescent image $IM_F$ is made constant irrespective of a set value of the coefficient m, it is possible to appropriately evaluate the fluorescent image $IM_F$.

Further, fluorescent pixels and non-fluorescent pixels are identified by the identification unit 11 comparing pixel values of a plurality of pixels of fluorescent image data with a threshold value. According to such a configuration, it is possible to easily and accurately identify pixels included in a range of the fluorescent image using the fluorescent image data.

Also, the present invention is not limited to the above-described embodiment.

For example, various other methods can be adopted as a superimposed image data creation method by the image processing unit 13. That is, in a modified example of the present invention, the image processing unit 13 may use only background pixels as pixel data to be multiplied by a ratio of the coefficient m. Specifically, the image processing unit 13 calculates the following equation on the basis of the background image data $I_b(x, y)$, the coefficient m, and the parameter n to calculate each of the pixel values $I_B(x, y)$ of the background image data of the superimposition source.

$$I_B(x,y)=I_b(x,y)\times m\times(1-n)+I_b(x,y)\times n$$

That is, adjustment is performed by multiplying the pixel value $I_b(x, y)$ of the background pixel of the background image data by the coefficient m, and hence the background image data of the superimposition source is created.

Subsequently, the image processing unit 13 sets each of the pixel values $I_F(x, y)$ of the fluorescent image data of the superimposition source by calculating the following equation using the fluorescent image data $I_f(x, y)$ itself.

$$I_F(x,y)=I_f(x,y)$$

Further, the image processing unit 13 creates superimposed image data by superimposing the background image data of the superimposition source and the fluorescent image data of the superimposition source. Thereby, the pixel value $I_{SI}(x, y)$ of the superimposed image data in the fluorescent pixel is set to a value calculated by the following equation, and the background image and the fluorescent image are superimposed at a luminance ratio of 1:1.

$$I_{SI}(x,y)=I_b(x,y)+I_f(x,y)$$

On the other hand, the pixel value $I_{SI}(x, y)$ of the superimposed image data in the background pixel is set to a value calculated by the following equation, and the luminance of the background image is lowered corresponding to the coefficient m.

$$I_{SI}(x,y)=I_b(x,y)\times m+I_f(x,y)\approx I_b(x,y)\times m$$

Further, in the above-described embodiment, the coefficient m is set to $0 \leq m \leq 1$, but is not limited to this value range. That is, if the pixel value of the fluorescent image in the fluorescent image data is smaller than the pixel value of the background image in the background image data, for example, if image data obtained by inverting the luminance value of the image data obtained from the image sensor 3b is processed, $1 \leq m$ may be set as the coefficient m. In the above-described embodiment, by using such a coefficient m, the fluorescent image data $I_F(x, y)$ of the superimposition source can be created by summing the pixel value $I_f(x, y)$ of each pixel and a pixel value of a fluorescent pixel of the background image data $I_b(x, y)$ whose ratio (1-m) is adjusted so that it is decreased in accordance with an increasing rate of the luminance indicated by the coefficient m. Thereby, it is possible to compensate for an increased pixel value of the background image data of the superimposition source in a fluorescent pixel by using a pixel value of the fluorescent image data of the superimposition source.

Also, the fluorescent image acquisition system 1 is not limited to the form in which the camera unit 7 includes the imaging device 3 and the light emitting device 5, and the imaging device 3 and the light emitting device 5 may be adopted as separated devices. Switching ON/OFF of the emission of the excitation light $L_1$ by the light emitting device 5 is not limited to switching by the light source 5a, and the light emitting device 5 may include a shutter (not illustrated) that receives the excitation light $L_1$ emission from the light source 5a, and the ON/OFF of the emission of the excitation light $L_1$ toward the observation object P may be switched by the shutter.

Here, in the superimposed image creation apparatus and the superimposed image creation method, it is preferable to calculate values obtained by summing pixel values of non-fluorescent pixels of fluorescent image data and values obtained by multiplying pixel values of non-fluorescent pixels of background image data by a coefficient as pixel values of non-fluorescent pixels of a superimposed image in the image processing unit and the calculation step. If this configuration is provided, it is possible to improve minuteness of the image in the vicinity of a boundary of the fluorescent image because the fluorescent image data is applied to the non-fluorescent pixel in the superimposed image.

Also, in the image processing unit and the creation step, it is preferable to calculate a difference between first image data and second image data to create the fluorescent image data and the background image data using the second image data. If this image processing unit is provided, it is possible to extract a fluorescent image in the fluorescent image data and create background image data including only a background image.

Further, in the image processing unit and the calculation step, it is preferable to multiply pixel values of the pixels including the fluorescent pixels and the non-fluorescent pixels of the background image data by the coefficient to create background image data of a superimposition source, sum pixel values of the fluorescent image data and pixel values of the fluorescent pixels of the background image data adjusted to be increased in accordance with a decreasing rate indicated by the coefficient to create fluorescent image data of the superimposition source, and superimpose background image data of a superimposition source and fluorescent image data of the superimposition source to create the superimposed image. In this case, the background image data of the superimposition source and the fluorescent image data of the superimposition source are superimposed, and a superimposed image in which values, which are obtained by summing pixel values of fluorescent pixels of the fluorescent image data and pixel values of fluorescent pixels of the background image data at a ratio of 1:1, are designated as pixel values of the fluorescent pixels and values, which are obtained by adding values obtained by multiplying pixel values of non-fluorescent pixels of the background image data by a coefficient to pixel values of non-fluorescent pixels of the fluorescent image data, are designated as pixel values of the non-fluorescent pixels can be created.

Further, in the image processing unit and the calculation step, it is preferable to multiply the pixel values of the non-fluorescent pixels of the background image data by the coefficient to create background image data of a superimposition source and superimpose the background image data of the superimposition source and the fluorescent image data to create the superimposed image. According to this configuration, the background image data of the superimposition source and the fluorescent image data are superimposed and the superimposed image can be created by designating values, which are obtained by summing pixel values of fluorescent pixels of the fluorescent image data and pixel values of fluorescent pixels of the background image data at a ratio of 1:1, as pixel values of the fluorescent pixels and designating values, which are obtained by adding values obtained by multiplying pixel values of non-fluorescent pixels of the background image data by a coefficient to pixel values of non-fluorescent pixels of the fluorescent image data, as pixel values of the non-fluorescent pixels.

Further, it is preferable that the pixel value of the fluorescent image in the fluorescent image data be greater than the pixel value of the background image in the background image data. In the coefficient setting unit and the setting step, it is preferable to set the coefficient to a value greater than or equal to 0 and less than or equal to 1. According to this configuration, if image data of the fluorescent image having a larger pixel value than that of the background image is used, it is possible to conspicuously maintain luminance of a fluorescent image with respect to a background image.

Also, it is preferable that the pixel value of the fluorescent image in the fluorescent image data be less than the pixel value of the background image in the background image data. In the coefficient setting unit and the setting step, it is preferable to set the coefficient to a value greater than or equal to 1. In this case, if image data of the fluorescent image having a smaller pixel value than that of the background image is used, it is possible to conspicuously maintain luminance of a fluorescent image with respect to a background image.

Further, in the identification unit and the identification step, pixel values of the plurality of pixels of the fluorescent image data are compared with a threshold value to identify the fluorescent pixel and the non-fluorescent pixel. In this manner, it is possible to easily and accurately identify pixels included in a range of a fluorescent image using fluorescent image data.

INDUSTRIAL APPLICABILITY

A form of the present invention is applied to a superimposed image creation apparatus and a superimposed image creation method for creating an image in which a background image is superimposed on a fluorescent image of an object to be measured. According to the present invention, it is possible to more easily recognize the fluorescent image in the superimposed image in which the fluorescent image and the background image are superimposed.

REFERENCE SIGNS LIST

1 Fluorescent image acquisition system
3 Imaging device (capturing unit)
5 Light emitting device (light irradiating unit)
11 Identification unit
13 Image processing unit
19 Input device (coefficient setting unit)
P Observation object

The invention claimed is:

1. An apparatus for superimposing a fluorescent image of an object and a background image to create a superimposed image, the apparatus comprising:
   a light source configured to emit excitation light toward the object during a first period and stopping the emission of the excitation light during a second period;
   an image sensor having a plurality of pixels that are two-dimensionally arranged and configured to capture image of the object during each of the first period and the second period, and output first image data and second image data;
   processor configured to set a coefficient for adjusting a luminance value of the background image in the superimposed image,
   create fluorescent image data including the fluorescent image and background image data including the background image based on the first image data and the second image data, and
   identify fluorescent pixels, which are pixels constituting the fluorescent image, and non-fluorescent pixels, which are pixels other than the fluorescent pixels, among the plurality of pixels using the fluorescent image data,
   wherein the processor is configured to calculate values, which are obtained by summing pixel values of the fluorescent pixels of the fluorescent image data and pixel values of the fluorescent pixels of the background image data at a ratio of 1:1, as pixel values of the fluorescent pixels of the superimposed image and calculate values, which are obtained by multiplying at least pixel values of the non-fluorescent pixels of the background image data by the coefficient, as pixel values of the non-fluorescent pixels of the superimposed image to create the superimposed image.

2. The apparatus according to claim 1, wherein the processor is configured to calculate values, which are obtained by summing pixel values of the non-fluorescent pixels of the fluorescent image data and the values obtained by multiplying the pixel values of the non-fluorescent pixels of the background image data by the coefficient, as pixel values of the non-fluorescent pixels of the superimposed image.

3. The apparatus according to claim 1, wherein the processor is configured to calculate a difference between the first image data and the second image data to create the fluorescent image data and create the background image data using the second image data.

4. The apparatus according to claim 2, wherein the processor is configured to multiply pixel values of the pixels including the fluorescent pixels and the non-fluorescent pixels of the background image data by the coefficient to create background image data of a superimposition source, sum pixel values of the fluorescent image data and pixel values of the fluorescent pixels of the background image data adjusted to be increased in accordance with a decreasing rate indicated by the coefficient to create fluorescent image data of the superimposition source, and superimpose the background image data of the superimposition source and the fluorescent image data of the superimposition source to create the superimposed image.

5. The apparatus according to claim 2, wherein the processor is configured to multiply the pixel values of the non-fluorescent pixels of the background image data by the coefficient to create background image data of a superimposition source and superimpose the background image data of the superimposition source and the fluorescent image data to create the superimposed image.

6. The apparatus according to claim 1, wherein the pixel value of the fluorescent image in the fluorescent image data is greater than the pixel value of the background image in the background image data, and the processor is configured to set the coefficient to a value greater than or equal to 0 and less than or equal to 1.

7. The apparatus according to claim 1, wherein the pixel value of the fluorescent image in the fluorescent image data is less than the pixel value of the background image in the background image data, and the processor is configured to set the coefficient to a value greater than or equal to 1.

8. The apparatus according to claim 1, wherein the processor is configured to compare pixel values of the plurality of pixels of the fluorescent image data with a threshold value to identify the fluorescent pixel and the non-fluorescent pixel.

9. A method for superimposing a fluorescent image of an object and a background image to create a superimposed image, the method comprising:
   emitting excitation light toward the object during a first period and stopping the emission of the excitation light during a second period;
   capturing image of the object during each of the first period and the second period using an image sensor having a plurality of pixels that are two-dimensionally arranged and outputting first image data and second image data;
   setting a coefficient for adjusting a luminance value of the background image in the superimposed image;
   creating fluorescent image data including the fluorescent image and background image data including the background image based on the first image data and the second image data;
   identifying fluorescent pixels, which are pixels constituting the fluorescent image, and non-fluorescent pixels, which are pixels other than the fluorescent pixels, among the plurality of pixels using the fluorescent image data; and
   calculating values, which are obtained by summing pixel values of the fluorescent pixels of the fluorescent image data and pixel values of the fluorescent pixels of the background image data at a ratio of 1:1, as pixel values of the fluorescent pixels of the superimposed image and calculating values, which are obtained by multiplying at least pixel values of the non-fluorescent pixels of the background image data by the coefficient, as pixel values of the non-fluorescent pixels of the superimposed image to create the superimposed image.

10. The method according to claim 9, further comprising calculating values, which are obtained by summing pixel values of the non-fluorescent pixels of the fluorescent image data and the values obtained by multiplying the pixel values of the non-fluorescent pixels of the background image data by the coefficient, as pixel values of the non-fluorescent pixels of the superimposed image.

11. The method according to claim 9, further comprising calculating a difference between the first image data and the second image data to create the fluorescent image data and creating the background image data using the second image data.

12. The method according to claim 10, further comprising multiplying pixel values of the pixels including the fluorescent pixels and the non-fluorescent pixels of the background image data by the coefficient to create background image data of a superimposition source, summing pixel values of the fluorescent image data and pixel values of the fluorescent pixels of the background image data adjusted to be increased in accordance with a decreasing rate indicated by the coefficient to create fluorescent image data of the superimposition source, and superimposing the background image data of the superimposition source and the fluorescent image data of the superimposition source to create the superimposed image.

13. The method according to claim 10, further comprising multiplying the pixel values of the non-fluorescent pixels of the background image data by the coefficient to create background image data of a superimposition source and superimposing the background image data of the superimposition source and the fluorescent image data to create the superimposed image.

14. The method according to claim 9, wherein the pixel value of the fluorescent image in the fluorescent image data is greater than the pixel value of the background image in the background image data, and the setting sets the coefficient to a value greater than or equal to 0 and less than or equal to 1.

15. The method according to claim 9, wherein the pixel value of the fluorescent image in the fluorescent image data is less than the pixel value of the background image in the background image data, and the setting sets the coefficient to a value greater than or equal to 1.

16. The method according to claim 9, further comprising comparing pixel values of the plurality of pixels of the fluorescent image data with a threshold value to identify the fluorescent pixel and the non-fluorescent pixel.

17. The apparatus according to claim 3, wherein the processor is configured to multiply pixel values of the pixels including the fluorescent pixels and the non-fluorescent pixels of the background image data by the coefficient to create background image data of a superimposition source, sum pixel values of the fluorescent image data and pixel values of the fluorescent pixels of the background image data adjusted to be increased in accordance with a decreasing rate indicated by the coefficient to create fluorescent image data of the superimposition source, and superimpose the background image data of the superimposition source and the fluorescent image data of the superimposition source to create the superimposed image.

18. The apparatus according to claim 3, wherein the processor is configured to multiply the pixel values of the non-fluorescent pixels of the background image data by the coefficient to create background image data of a superimposition source and superimpose the background image data of the superimposition source and the fluorescent image data to create the superimposed image.

* * * * *